US011451366B2

(12) United States Patent
Chen (10) Patent No.: US 11,451,366 B2
(45) Date of Patent: Sep. 20, 2022

(54) LEAD-ON DETECTION CIRCUITRY OF BIOPOTENTIAL ACQUISITION SYSTEM

(71) Applicant: MEDIATEK INC., Hsin-Chu (TW)

(72) Inventor: Chih-Hsin Chen, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 41 days.

(21) Appl. No.: 17/111,474

(22) Filed: Dec. 3, 2020

(65) Prior Publication Data

US 2021/0226764 A1    Jul. 22, 2021

Related U.S. Application Data

(60) Provisional application No. 62/961,947, filed on Jan. 16, 2020.

(51) Int. Cl.
| | |
|---|---|
| *H04L 7/00* | (2006.01) |
| *H03K 3/017* | (2006.01) |
| *H03K 5/24* | (2006.01) |
| *H03D 7/00* | (2006.01) |

(52) U.S. Cl.
CPC ........... *H04L 7/0012* (2013.01); *H03K 3/017* (2013.01); *H03K 5/24* (2013.01); *H03D 7/00* (2013.01)

(58) Field of Classification Search
CPC ........ H04L 7/0012; H03K 3/017; H03K 5/24; A61N 1/37223; A61N 2001/083; A61N 1/36017; A61N 1/36034; A61B 5/053; A61B 5/24; A61B 5/25; A61B 5/05; A61B 5/0093
See application file for complete search history.

(56) References Cited

U.S. PATENT DOCUMENTS

| | | | |
|---|---|---|---|
| 5,368,041 A | 11/1994 | Shambroom | |
| 5,912,586 A | 6/1999 | Mitzlaff | |
| 11,051,707 B2 * | 7/2021 | Felix | .................... A61B 5/0245 |
| 2012/0157807 A1 | 6/2012 | Virtanen | |

(Continued)

FOREIGN PATENT DOCUMENTS

| | | |
|---|---|---|
| EP | 2 818 103 A1 | 12/2014 |
| WO | 2015/061459 A1 | 4/2015 |

OTHER PUBLICATIONS

Texas Instruments, "ADS129x Low-Power, 8-Channel, 24-Bit Analog Front-End for Biopotential Measurements"; https://www.ti.com/lit/ds/symlink/ads1294.pdf?ts=1606195987977&ref_url=https%253A%252F%252Fwww.ti.com%252Fproduct%252FADS1294 ,Aug. 2015.

(Continued)

*Primary Examiner* — Khanh C Tran
(74) *Attorney, Agent, or Firm* — Winston Hsu (57) ABSTRACT

The present invention provides a lead-on detection circuitry of a biopotential acquisition system. The lead-on detection circuitry includes an input terminal, a duty-cycle controller, a transmitting signal generator and a mixer-based receiver. The duty-cycle controller is configured to generate a first clock signal. The transmitting signal generator is configured to generate a transmitting signal to the input terminal according to the first clock signal. The mixer-based receiver is configured to perform a mixing operation based on the first clock signal and the transmitting signal to generate an output signal, wherein the output signal indicates if an electrode of the biopotential acquisition system is in contact with a human body, and the electrode is coupled to the input terminal.

10 Claims, 6 Drawing Sheets

(56) References Cited

U.S. PATENT DOCUMENTS

| | | | | |
|---|---|---|---|---|
| 2012/0323132 A1* | 12/2012 | Warner | ............... | G16H 40/63 |
| | | | | 600/509 |
| 2016/0028388 A1* | 1/2016 | Kim | ............... | H03F 3/00 |
| | | | | 327/114 |
| 2019/0380654 A1* | 12/2019 | Felix | ............... | A61B 5/7214 |
| 2020/0037877 A1* | 2/2020 | Ott | ............... | A61B 5/0006 |

OTHER PUBLICATIONS

Maxim Integrated Products,"Ultra-Low-Power, Single-Channel Integrated Biopotential (ECG, R-to-R, and Pace Detection) and Bioimpedance (BioZ) AFE"; https://datasheets.maximintegrated.com/en/ds/MAX30001.pdf ,2019.

Analog Devices, "50uA, 2mm*1.7mm WLCSP, Low Noise, Heart Rate Monitor for Wearable Products" https://www.analog.com/media/en/technical-documentation/data-sheets/ad8233.pdf ,2020.

* cited by examiner

LEAD-ON DETECTION CIRCUITRY OF BIOPOTENTIAL ACQUISITION SYSTEM

CROSS REFERENCE TO RELATED APPLICATIONS

This application claims the priority of U.S. Provisional Application No. 62/961,947, filed on Jan. 16, 2020, which is included herein by reference in its entirety.

BACKGROUND

A conventional medical device generally uses large dry electrodes or wet electrodes to measure physiological signals to obtain physiological features such as bio-impedance or electrocardiography. Recently, personal biosensors such as portable/wearable medical devices become popular for providing physiological information at all time for the reference to the user. Considering the use and design of these portable medical devices, smaller dry electrodes are more appropriate. However, smaller dry electrode means worse electrode impedance, and the worse electrode impedance (i.e. large electrode impedance) may cause detection error of a lead-on detection procedure of the medical device.

Specifically, a physiological information detection circuitry is disabled to lower power consumption when electrodes of the portable medical device are not in contact with a human body. The portable medical device has a lead-on detection circuitry for always detecting if the electrodes are in contact with the human body, and once the lead-on detection circuitry determines that the electrodes are in contact with the human body, the lead-on detection circuitry sends a trigger signal to enable the physiological information detection circuitry to measure physiological signals to obtain the physiological features of the human body. Because of the smaller dry electrodes used in the portable medical device, the lead-on detection circuitry may suffer detection errors due to the large impedance of the electrodes, a power line common mode interference (e.g. 60 Hz interference) and an electrode tissue offset (i.e., a DC offset existing between skin and electrodes), causing the lead-on detection circuitry and the physiological information detection circuitry to have wrong actions.

In addition, because the lead-on detection circuitry are always enabled to determine if the electrodes are in contact with the human body, the lead-on detection circuitry causes a burden on power of the portable medical device.

SUMMARY

It is therefore an objective of the present invention to provide a lead-on detection circuitry, which can accurately determine if the small dry electrodes are in contact with the human body, to solve the above-mentioned problems.

According to one embodiment of the present invention, a lead-on detection circuitry of a biopotential acquisition system is disclosed. The lead-on detection circuitry comprises an input terminal, a duty-cycle controller, a transmitting signal generator and a mixer-based receiver. The duty-cycle controller is configured to generate a first clock signal. The transmitting signal generator is configured to generate a transmitting signal to the input terminal according to the first clock signal. The mixer-based receiver is configured to perform a mixing operation based on the first clock signal and the transmitting signal to generate an output signal, wherein the output signal indicates if an electrode of the biopotential acquisition system is in contact with a human body, and the electrode is coupled to the input terminal.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular system components. As one skilled in the art will appreciate, manufacturers may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". The terms "couple" and "couples" are intended to mean either an indirect or a direct electrical connection. Thus, if a first device couples to a second device, that connection may be through a direct electrical connection, or through an indirect electrical connection via other devices and connections.

Figure 1:
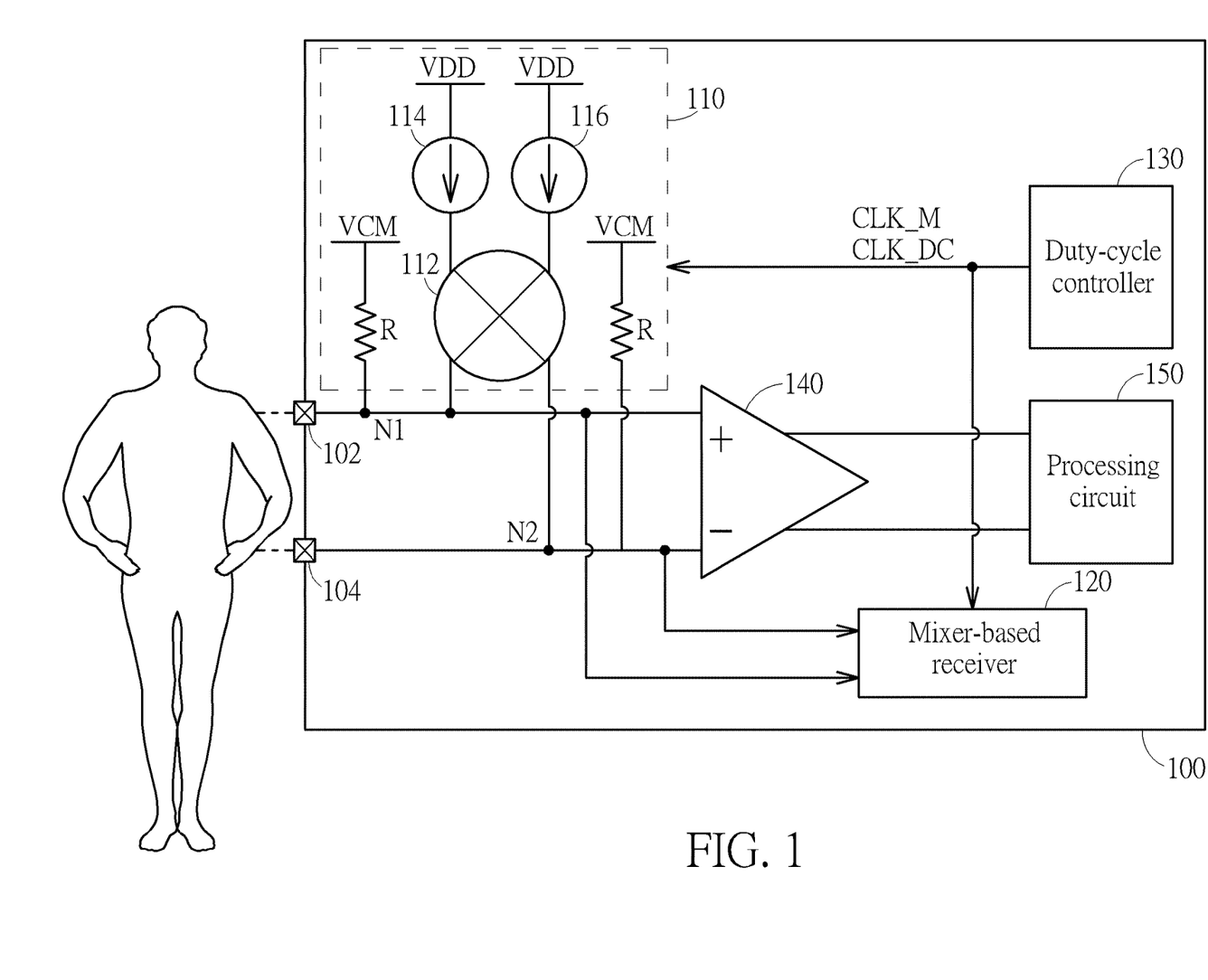
FIG. 1 is a diagram illustrating a biopotential acquisition system according to one embodiment of the present invention.

FIG. 1 is a diagram illustrating a biopotential acquisition system 100 according to one embodiment of the present invention. As shown in FIG. 1, the biopotential acquisition system 100 is a two-electrode biopotential acquisition system having two electrodes 102 and 104, and the electrodes 102 and 104 are used to connect to a right body (e.g. right hand) and a left body (e.g. left hand) to obtain biopotential signals of a human body, and the biopotential acquisition system 100 can process and analyze the biopotential signals to determine physiological signals such as electrocardiography (ECG) signals, and the physiological features can be displayed on a screen of the biopotential acquisition system 100. In this embodiment, the biopotential acquisition system 100 can be built in any portable electronic device or a wearable electronic device.

In order to save the power consumption of the biopotential acquisition system 100, the biopotential acquisition system 100 comprises a lead-on detection circuitry to determine if the electrodes 102 and 104 are in contact with the human body. Specifically, the biopotential acquisition system 100 can operate in a normal mode and a standby mode, wherein when biopotential acquisition system 100 operates in the standby mode, part of the circuits are disabled to lower the power consumption, at this time the lead-on detection circuitry is enabled to detect if the electrodes 102 and 104 are in contact with the human body. Once the lead-on detection circuitry determines that the electrodes 102 and 104 are in contact with the human body, the biopotential acquisition system 100 is controlled from the standby mode to the normal mode, and a power amplifier 140 starts to receive input signals (biopotential signals) from the electrodes 102 and 104 to generate an amplified signal to a processing circuit 150 for determining the physiological information.

Because the invention focuses on the lead-on detection circuitry, the following description only describes the lead-on detection circuitry of the biopotential acquisition system 100. As shown in FIG. 1, the lead-on detection circuitry comprises two input terminals N1 and N2, a transmitting signal generator 110, a mixer-based receiver 120 and a duty-cycle controller 130. The input terminal N1 is connected to the electrode 102, and the input terminal N2 is connected to the electrode 104. The transmitting signal generator 110 comprises a mixer 112, two current sources 114 and 116 and two resistors R, wherein the current sources are coupled between a supply voltage VDD and the mixer 112, and the resistor R is coupled between the input terminal N1/N2 and a common mode voltage VCM. In the operation of the lead-on detection circuitry, the duty-cycle controller 130 generates at least a clock signal CLK_M to the transmitting signal generator 110, and the mixer 112 receives the clock signal CLK_M to generate transmitting signals to the input terminals N1 and N2. In this embodiment, a frequency of the clock signal CLK_M may be several hundred hertz (Hz) or several kilohertz (kHz), for example, the frequency may be ranging from 200 Hz to 4 kHz. In addition, a frequency of the transmitting signals is equal to the frequency of the clock signal CLK_M. Then, the mixer-based receiver 120 receives the transmitting signals from the input terminals N1 and N2, and the mixer-based receiver 120 mixes the transmitting signals with the lock signal CLK_M to generate DC signals, and an output signal Vout is generated based on the DC signals.

In the embodiment shown in FIG. 1, the DC signals generated by mixing the transmitting signals with the clock signal CLK_M can accurately reflect the voltages at the input terminals N1 and N2, therefore, the mixer-based receiver 120 can refer to levels of the DC signals to generate the output signal Vout for determining if the electrodes 102 and 104 are in contact with the human body.

In one embodiment, the duty-cycle controller 130 may further generate a clock signal CLK_DC to enable or disable the transmitting signal generator 110 and the mixer-based receiver 120. A frequency of the clock signal CLK_DC may be much slower than the frequency of the clock signal CLK_M, for example, a cycle of the clock signal CLK_DC may be 0.5 to 2 seconds, or any response time or delay time acceptable to the user. That is, if one cycle of the clock signal CLK_DC is 0.5 seconds, the transmitting signal generator 110 and the mixer-based receiver 120 are enabled for a short time every 0.5 seconds, wherein the short time that the transmitting signal generator 110 and the mixer-based receiver 120 are enabled is shorter or much shorter than 0.5 seconds, for example, twenty milliseconds. In addition, the clock signal CLK_M is generated to the transmitting signal generator 110 and the mixer-based receiver 120 only when the clock signal CLK_DC has an enablement period (e.g. high voltage level). By using the above control mechanism using the clock signal CLK_DC, the lead-on detection circuitry can greatly reduce the power consumption.

Figure 2:
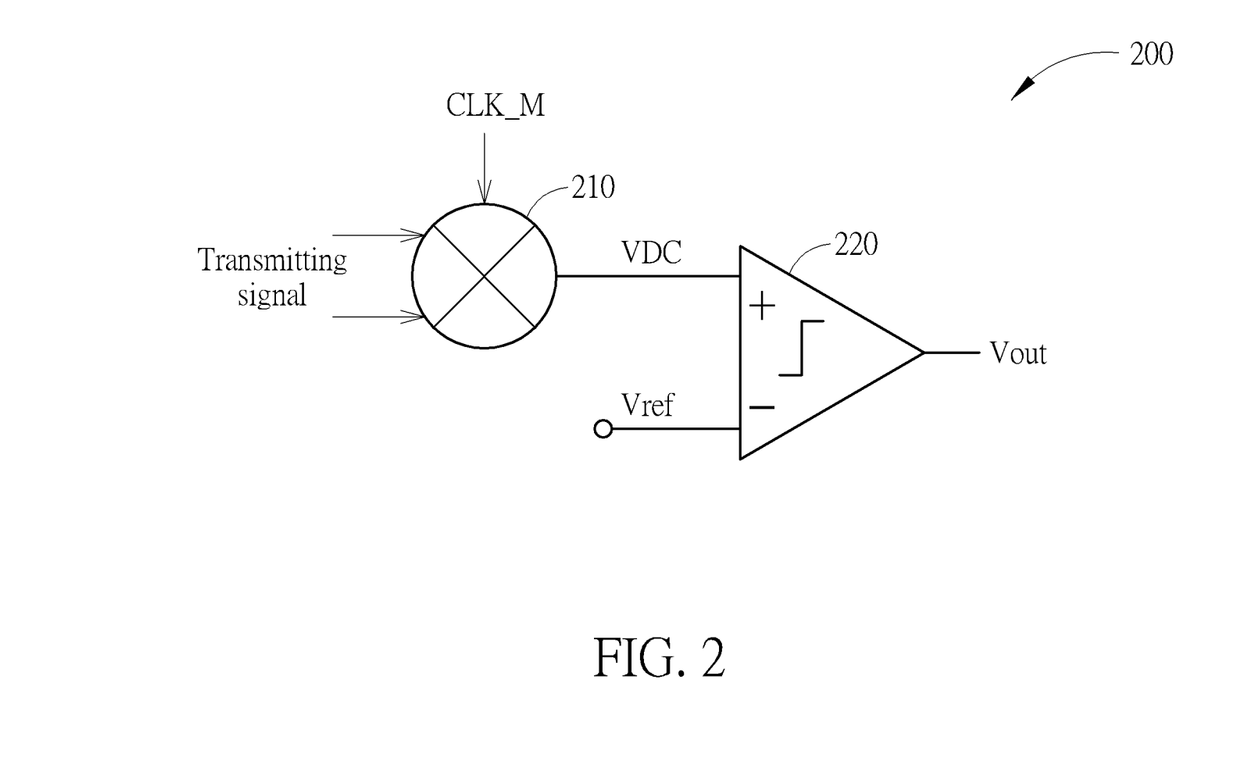
FIG. 2 is a diagram illustrating a mixer-based receiver according to a first embodiment of the present invention.

FIG. 2 is a diagram illustrating a mixer-based receiver 200 according to one embodiment of the present invention, wherein the mixer-based receiver 200 can be used to implement the mixer-based receiver 120 shown in FIG. 1. The mixer-based receiver 200 comprises a mixer 210 and a comparator 220. During the operation of the mixer-based receiver 200, the mixer 210 receives the transmitting signals from the input terminals N1 and N2 and the clock signal CLK_M from the duty-cycle controller 130, and the mixer 210 mixes the transmitting signals and the clock signal CLK_M having the same frequency to generate a mixed signal VDC. The mixed signal VDC mainly contains DC component, so the mixed signal VDC can be regarded as the DC signal. Then, the comparator 220 compares the mixed signal VDC with a reference signal Vref to generate the output signal Vout, wherein the Vout can be used to determine if the electrodes 102 and 104 are in contact with the human body. In one embodiment, if the output signal Vout indicates that the mixed signal VDC is greater than the reference signal Vref, it means that the electrodes 102 and 104 are not in contact with the human body; and if the output signal Vout indicates that the mixed signal is less than the reference signal Vref, it means that the electrodes 102 and 104 are in contact with the human body.

Figure 3:
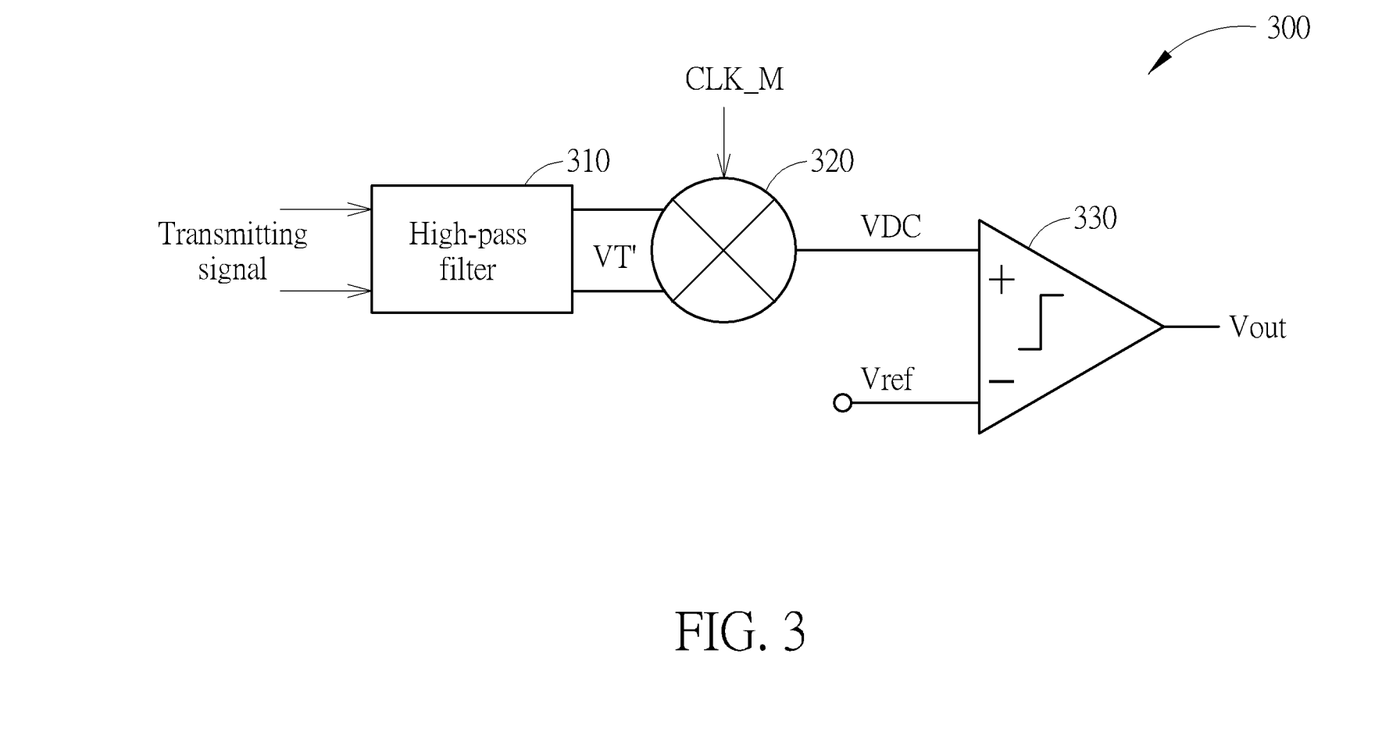
FIG. 3 is a diagram illustrating a mixer-based receiver according to a second embodiment of the present invention.

FIG. 3 is a diagram illustrating a mixer-based receiver 300 according to one embodiment of the present invention, wherein the mixer-based receiver 300 can be used to implement the mixer-based receiver 120 shown in FIG. 1. The mixer-based receiver 300 comprises a high-pass filter 310, a mixer 320 and a comparator 330. During the operation of the mixer-based receiver 300, the high-pass filter 310 receives the transmitting signals from the input terminals N1 and N2, and the high-pass filter 310 performs a high-pass filtering operation on the transmitting signals to generate a filtered signal VT'. The mixer 320 mixes the filtered signal VT' and the clock signal CLK_M to generate a mixed signal VDC. The mixed signal VDC mainly contains DC component, so the mixed signal VDC can be regarded as the DC signal. Then, the comparator 330 compares the mixed signal VDC with a reference signal Vref to generate the output signal Vout, wherein the Vout can be used to determine if the electrodes 102 and 104 are in contact with the human body. In the embodiment shown in FIG. 3, the transmitting signals may have an electrode tissue offset (i.e., a DC offset existing between skin and electrodes) when the human body contacts to the electrodes 102 and 104, so the high-pass filter 310 is configured to block the electrode tissue offset, that is the high-pass filter 310 prevents the electrode tissue offset from affecting the operation of the comparator 330. Therefore, the output voltage Vout will be more accurate.

Figure 4:
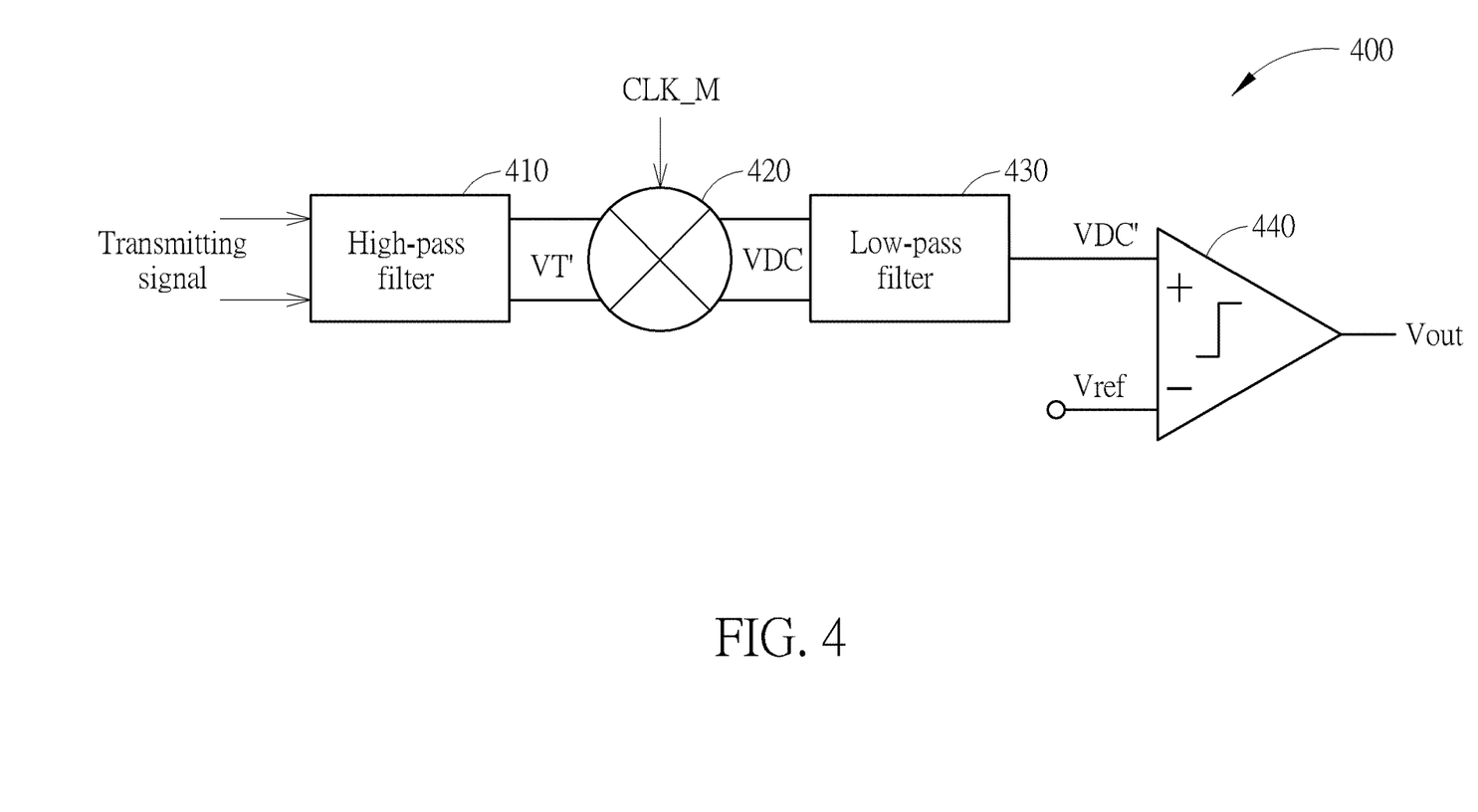
FIG. 4 is a diagram illustrating a mixer-based receiver according to a third embodiment of the present invention.

FIG. 4 is a diagram illustrating a mixer-based receiver 400 according to one embodiment of the present invention, wherein the mixer-based receiver 400 can be used to implement the mixer-based receiver 120 shown in FIG. 1. The mixer-based receiver 400 comprises a high-pass filter 410, a mixer 420, a low-pass filter 430 and a comparator 440. During the operation of the mixer-based receiver 400, the high-pass filter 410 receives the transmitting signals from the input terminals N1 and N2 and filters the transmitting signals to generate a filtered signal VT'. The mixer 420 mixes the filtered signal VT' and the clock signal CLK_M to generate a mixed signal VDC. The low-pass filter 430 filters the DC signal VDC to generate a filtered mixed signal VDC'. Then, the comparator 440 compares the filtered mixed signal VDC' with a reference signal Vref to generate the output signal Vout, wherein the Vout can be used to determine if the electrodes 102 and 104 are in contact with the human body. In the embodiment shown in FIG. 4, the high-pass filter 410 is configured to block the electrode tissue offset, that is the high-pass filter 410 prevents the electrode tissue offset from affecting the operation of the comparator 440. In addition, the low-pass filter 430 is configured to reduce the power line interference (e.g. 60 Hz interference) and other noise such as part the electrode tissue offset is modulated to high frequency, so that the filtered mixed signal VDC' generated by the low-pass filter 430 can be regarded as a DC signal. Therefore, the output voltage Vout will be more accurate.

Figure 5:
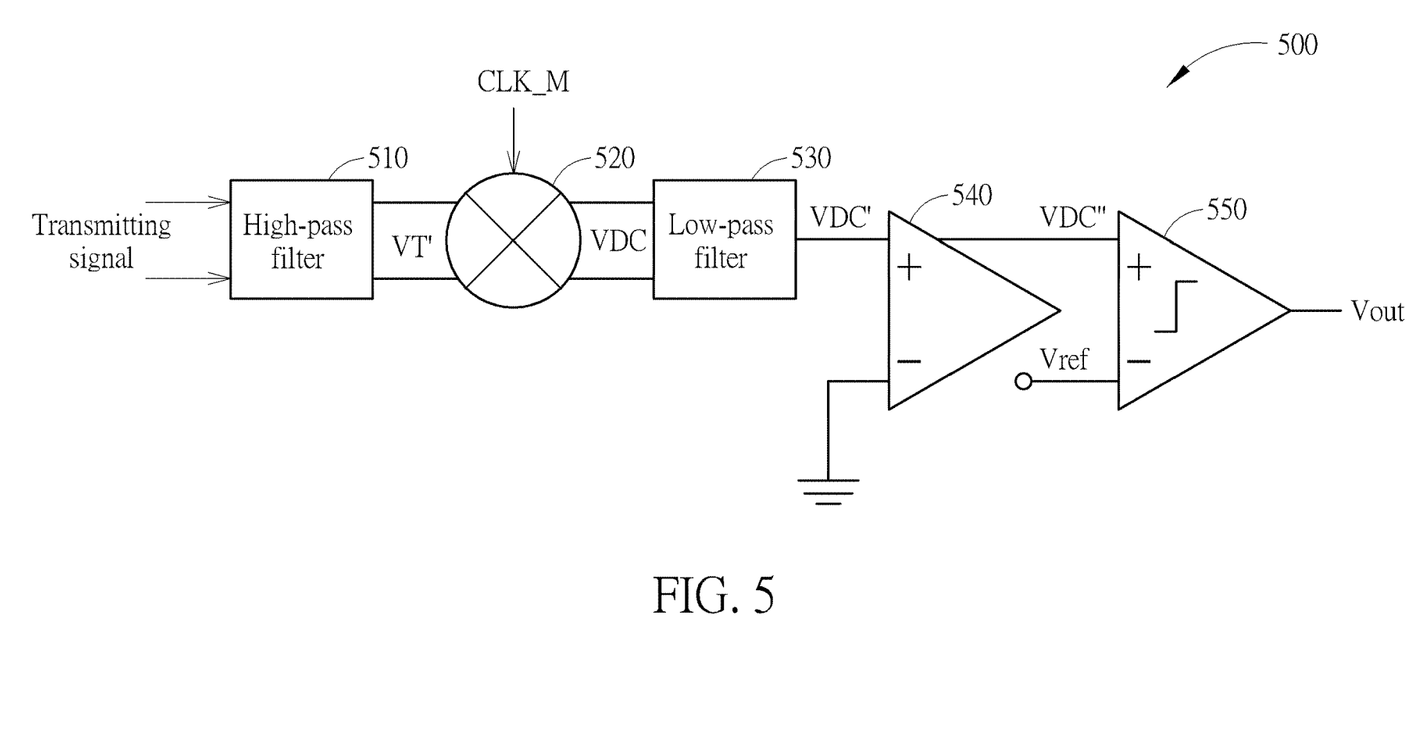
FIG. 5 is a diagram illustrating a mixer-based receiver according to a fourth embodiment of the present invention.

FIG. 5 is a diagram illustrating a mixer-based receiver 500 according to one embodiment of the present invention, wherein the mixer-based receiver 500 can be used to implement the mixer-based receiver 120 shown in FIG. 1. The mixer-based receiver 500 comprises a high-pass filter 510, a mixer 520, a low-pass filter 530, an amplifier 540 and a comparator 550. During the operation of the mixer-based receiver 500, the high-pass filter 510 receives the transmitting signals from the input terminals N1 and N2 and filters the transmitting signals to generate a filtered signal VT'. The mixer 520 mixes the filtered signal VT' and the clock signal CLK_M to generate a mixed signal VDC. The low-pass filter 530 filters the mixed signal VDC to generate a filtered mixed signal VDC'. The amplifier 540 amplifies the filtered mixed signal VDC' to generate an amplified signal VDC". Then, the comparator 550 compares the amplified signal VDC" with a reference signal Vref to generate the output signal Vout, wherein the Vout can be used to determine if the electrodes 102 and 104 are in contact with the human body. In the embodiment shown in FIG. 5, the high-pass filter 510 is configured to block the electrode tissue offset, that is the high-pass filter 510 prevents the electrode tissue offset from affecting the operation of the comparator 540. The low-pass filter 530 is configured to reduce the power line interference (e.g. 60 Hz interference) and other noise such as part the electrode tissue offset is modulated to high frequency. In addition, the amplifier 540 serving as a gain stage can increase sensitivity of the mixer-based receiver 500. Therefore, the output voltage Vout will be more accurate.

In other embodiments of the present invention, the high-pass filter 410 shown in FIG. 4 can be removed from the mixer-based receiver 400, and the high-pass filter 450 shown in FIG. 5 can be removed from the mixer-based receiver 500, and the output voltage Vout may also has enough accuracy due to the operation of the low-pass filter 430/530.

Figure 6:
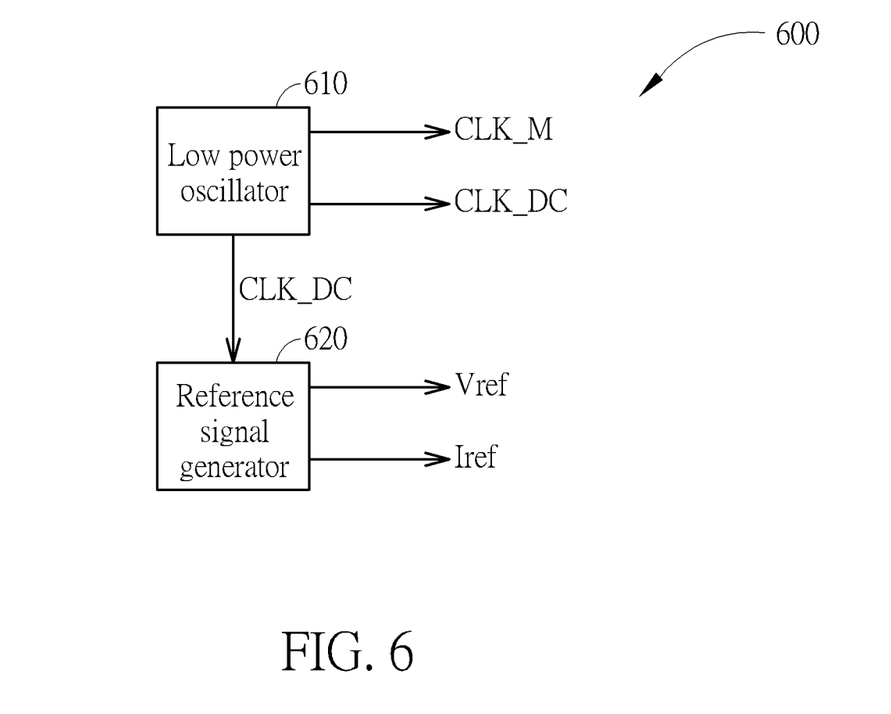
FIG. 6 is a diagram illustrating a duty-cycle controller according to one embodiment of the present invention.

FIG. 6 is a diagram illustrating a duty-cycle controller 600 according to one embodiment of the present invention, wherein the duty-cycle controller 600 can be used to implement the duty-cycle controller 130 shown in FIG. 1. The duty-cycle controller 600 comprises a low power oscillator 610 and a reference signal generator 620. During operation of the duty-cycle controller 600, the low power oscillator 610 is configured to generate the clock signal CLK_M and the clock signal CLK_DC, and the reference signal generator 620 is configured to generate reference signals Vref and Iref to the transmitting signal generator 110 and the mixer-based receiver 130, wherein the reference signal Vref is a reference voltage, and the reference signal Iref is a reference current. In this embodiment, the reference signal generator 620 is enabled or disabled based on the clock signal CLK_DC, and the reference signals Vref and Iref are generated only when the clock signal CLK_DC has an enablement period (e.g. high voltage level). Therefore, the duty-cycle controller 600 can save large power in the standby mode.

It is noted that the transmitting signal generator 110 shown in FIG. 1 is for illustrative purposes only, as long as the transmitting signal generator 110 can generate the transmitting signal whose frequency is determined based on the clock signal CLK_M, the transmitting signal generator 110 may have other circuit design. For example, the current sources 114 and 116 shown in FIG. 1 may be replaced by a voltage source design.

Briefly summarized, in the embodiments of the lead-on detection circuitry, the mixer-based receiver is used to determine if the small dry electrodes are in contact with the human body accurately. In addition, the duty-cycle controller provides a fast clock signal to the transmitting signal generator and the mixer-based receiver for the detection procedure, and the duty-cycle controller may further provide a slow clock signal for controlling the enablement of the transmitting signal generator and the mixer-based receiver to lower the power consumption. Therefore, the embodiment of the lead-on detection circuitry can work well with small power consumption.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A lead-on detection circuitry of a biopotential acquisition system, comprising:
    an input terminal;
    a duty-cycle controller, configured to generate a first clock signal;
    a transmitting signal generator, configured to generate a transmitting signal to the input terminal according to the first clock signal;
    a mixer-based receiver, configured to perform a mixing operation based on the first clock signal and the transmitting signal to generate an output signal, wherein the output signal indicates if an electrode of the biopotential acquisition system is in contact with a human body, and the electrode is coupled to the input terminal;
    wherein the mixer-based receiver comprises:
    a mixer, configured to generate a mixed signal according to the transmitting signal and the first clock signal; and
    a comparator, coupled to the mixer, configured to compare the mixed signal with a reference signal to generate the output signal.

2. The lead-on detection circuitry of claim 1, wherein the mixer is configured to mix the transmitting signal with the first clock signal to generate the mixed signal.

3. The lead-on detection circuitry of claim 1, wherein the mixer-based receiver further comprises:
    a high-pass filter, configured to perform a high-pass filtering operation on the transmitting signal to generate a filtered signal;
    wherein the mixer is configured to mix the filtered signal with the first clock signal to generate a mixed signal.

4. The lead-on detection circuitry of claim 1, wherein the mixer-based receiver comprises:
    a high-pass filter, configured to perform a high-pass filtering operation on the transmitting signal to generate a filtered signal;
    the mixer, coupled to the high-pass filter, configured to mix the filtered signal with the first clock signal to generate the mixed signal;
    a low-pass filter, coupled to the mixer, configured to perform a low-pass filtering operation on the mixed signal to generate a filtered mixed signal; and
    the comparator, configured to compare the filtered mixed signal with the reference signal to generate the output signal.

5. The lead-on detection circuitry of claim 1, wherein the mixer-based receiver comprises:
- a high-pass filter, configured to perform a high-pass filtering operation on the transmitting signal to generate a filtered signal;
- the mixer, coupled to the high-pass filter, configured to mix the filtered signal with the first clock signal to generate the mixed signal;
- a low-pass filter, coupled to the mixer, configured to perform a low-pass filtering operation on the mixed signal to generate a filtered mixed signal;
- an amplifier, coupled to the low-pass filter, configured to amplify the filtered mixed signal to generate an amplified signal; and
- the comparator, configured to compare the amplified signal with the reference signal to generate the output signal.

6. The lead-on detection circuitry of claim 1, wherein the mixer-based receiver comprises:
- the mixer, coupled to the high-pass filter, configured to mix the transmitting signal with the first clock signal to generate the mixed signal;
- a low-pass filter, coupled to the mixer, configured to perform a low-pass filtering operation on the mixed signal to generate a filtered mixed signal; and
- the comparator, configured to compare the filtered mixed signal with the reference signal to generate the output signal.

7. A lead-on detection circuitry of a biopotential acquisition system, comprising:
- an input terminal;
- a duty-cycle controller, configured to generate a first clock signal;
- a transmitting signal generator, configured to generate a transmitting signal to the input terminal according to the first clock signal;
- a mixer-based receiver, configured to perform a mixing operation based on the first clock signal and the transmitting signal to generate an output signal, wherein the output signal indicates if an electrode of the biopotential acquisition system is in contact with a human body, and the electrode is coupled to the input terminal;
- wherein the duty-cycle controller further generates a second clock signal, wherein a frequency of the second clock signal is lower than a frequency of the first clock signal; and the mixer-based receiver is enabled or disabled based on the second clock signal.

8. The lead-on detection circuitry of claim 7, wherein the transmitting signal generator receives the second clock signal, and the transmitting signal generator is enabled or disabled based on the second clock signal.

9. A lead-on detection circuitry of a biopotential acquisition system, comprising:
- an input terminal;
- a duty-cycle controller, configured to generate a first clock signal;
- a transmitting signal generator, configured to generate a transmitting signal to the input terminal according to the first clock signal;
- a mixer-based receiver, configured to perform a mixing operation based on the first clock signal and the transmitting signal to generate an output signal, wherein the output signal indicates if an electrode of the biopotential acquisition system is in contact with a human body, and the electrode is coupled to the input terminal;
- wherein the duty-cycle controller comprises:
- an oscillator, wherein the oscillator is configured to generate the first clock signal and a second clock signal, and a frequency of the second clock signal is lower than a frequency of the first clock signal; and
- a reference signal generator, configured to generate a reference signal to the transmitting signal generator or the mixer-based receiver;
- wherein the reference signal generator is enabled or disabled based on the second clock signal.

10. The lead-on detection circuitry of claim 9, wherein the mixer-based receiver or the transmitting signal generator is enabled or disabled based on the second clock signal.

* * * * *